(12) United States Patent
Xu et al.

(10) Patent No.: US 12,121,226 B2
(45) Date of Patent: *Oct. 22, 2024

(54) FLEXIBLE SURGICAL INSTRUMENT WITH STRUCTURAL BONES IN A CROSSED ARRANGEMENT

(71) Applicant: Beijing Surgerii Robotics Company Limited, Beijing (CN)

(72) Inventors: Kai Xu, Beijing (CN); Zhengchen Dai, Beijing (CN); TianLai Dong, Beijing (CN); Jiangran Zhao, Beijing (CN); Huan Liu, Beijing (CN); Bo Liang, Beijing (CN); Zhixiong Yang, Beijing (CN); Zhijun Zhu, Beijing (CN)

(73) Assignee: BEIJING SURGERII ROBOTICS COMPANY LIMITED, Beijing (CN)

( * ) Notice: Subject to any disclaimer, the term of this patent is extended or adjusted under 35 U.S.C. 154(b) by 268 days.

This patent is subject to a terminal disclaimer.

(21) Appl. No.: 17/648,411

(22) Filed: Jan. 19, 2022

(65) Prior Publication Data
US 2022/0142629 A1 May 12, 2022

Related U.S. Application Data

(63) Continuation of application No. 16/329,740, filed as application No. PCT/CN2017/099851 on Aug. 31, 2017, now Pat. No. 11,266,388.

(30) Foreign Application Priority Data

Aug. 31, 2016 (CN) .......................... 201610799314.1
Aug. 31, 2016 (CN) .......................... 201610799332.X

(51) Int. Cl.
*A61B 17/00* (2006.01)
*A61B 17/29* (2006.01)
(Continued)

(52) U.S. Cl.
CPC ........ *A61B 17/00234* (2013.01); *A61B 17/00* (2013.01); *A61B 17/29* (2013.01);
(Continued)

(58) Field of Classification Search
CPC .................. A61B 1/0057; A61B 34/71; A61B 2017/2905; A61B 2034/306; A61B 2034/715; B25J 9/065
See application file for complete search history.

(56) References Cited

U.S. PATENT DOCUMENTS

| | | | | |
|---|---|---|---|---|
| 7,686,826 | B2 * | 3/2010 | Lee ........................ | A61B 17/29 606/205 |
| 2002/0087048 | A1 | 7/2002 | Brock et al. | |

(Continued)

FOREIGN PATENT DOCUMENTS

| | | |
|---|---|---|
| CN | 103085083 A | 5/2013 |
| CN | 103315781 A | 9/2013 |

(Continued)

OTHER PUBLICATIONS

ISA State Intellectual Property Office of the People's Republic of China, International Search Report Issued in Application No. PCT/CN2017/099851, Dec. 7, 2017, WIPO, 4 pages.

(Continued)

*Primary Examiner* — Elizabeth Houston
*Assistant Examiner* — Lindsey Bachman
(74) *Attorney, Agent, or Firm* — McCoy Russell LLP

(57) ABSTRACT

The present disclosure generally relates to a surgical instrument. In some embodiments, the flexible surgical instrument, comprising: a distal structural body comprising first distal structural segment and second distal structural segment, the first distal structural segment comprising a first distal fixing disk and first distal segment structural backbones, the second distal structural segment comprising a
(Continued)

second distal fixing disk and second distal segment structural backbones; and a proximal structural body comprising a proximal structural segment, the proximal structural segment comprising a proximal fixing disk, first proximal segment structural backbones, and second proximal segment structural backbones, the first proximal segment structural backbones being connected to the first distal segment structural backbones in a crossed arrangement; or the second proximal segment structural backbones being connected to the second distal segment structural backbones in a crossed arrangement.

18 Claims, 11 Drawing Sheets

(51) Int. Cl.
    *A61B 34/30* (2016.01)
    *B25J 1/02* (2006.01)
    *B25J 19/02* (2006.01)

(52) U.S. Cl.
    CPC ................ *A61B 34/30* (2016.02); *B25J 1/02* (2013.01); *A61B 2017/00305* (2013.01); *A61B 2017/2905* (2013.01); *A61B 2017/2912* (2013.01); *A61B 2034/301* (2016.02); *B25J 19/02* (2013.01)

(56) References Cited

U.S. PATENT DOCUMENTS

| | | | |
|---|---|---|---|
| 2011/0163146 A1 | 7/2011 | Ortiz et al. | |
| 2013/0090763 A1 | 4/2013 | Simaan et al. | |
| 2015/0216546 A1 | 8/2015 | Krause et al. | |
| 2015/0352728 A1* | 12/2015 | Wang | B25J 18/06 74/490.04 |

FOREIGN PATENT DOCUMENTS

| | | |
|---|---|---|
| CN | 103707322 A | 4/2014 |
| CN | 103732161 A | 4/2014 |
| CN | 104883991 A | 9/2015 |
| CN | 104887313 A | 9/2015 |
| CN | 106175852 A | 12/2016 |
| CN | 106361387 A | 2/2017 |
| EP | 2008594 A2 | 12/2008 |
| JP | 2009136684 A | 6/2009 |
| JP | 2012525916 A | 10/2012 |
| WO | 9910137 A1 | 3/1999 |
| WO | 2006057702 A2 | 6/2006 |
| WO | 2009001054 A1 | 12/2008 |
| WO | 2011108840 A2 | 9/2011 |
| WO | 2015126752 A1 | 8/2015 |
| WO | 2015153111 A1 | 10/2015 |

OTHER PUBLICATIONS

State Intellectual Property Office of the People's Republic of China, First Search Issued in Application No. 201610799332.X, Mar. 16, 2018, 4 pages.

State Intellectual Property Office of the People's Republic of China, Office Action and Search Report Issued in Application No. 201610799314.1, May 3, 2018, 9 pages.

China National Intellectual Property Administration, Supplementary Search Issued in Application No. 201610799314.1, Dec. 7, 2018, 3 pages.

European Patent Office, Supplementary European Search Report Issued in Application No. 17845503.6, Apr. 6, 2020, Germany, 2 pages.

* cited by examiner

FLEXIBLE SURGICAL INSTRUMENT WITH STRUCTURAL BONES IN A CROSSED ARRANGEMENT

CROSS REFERENCE TO RELATED APPLICATIONS

The present application is a continuation of U.S. Non-Provisional patent application Ser. No. 16/329,740 entitled, "FLEXIBLE SURGICAL INSTRUMENT WITH STRUCTURAL BONES IN A CROSSED ARRANGEMENT", and filed Feb. 28, 2019. U.S. Non-Provisional patent application Ser. No. 16/329,740 is a U.S. National Phase of International Application No. PCT/CN2017/099851 filed on Aug. 31, 2017. International Application No. PCT/CN2017/099851 claims priority to Chinese Patent Application No. 201610799314.1 filed on Aug. 31, 2016, and Chinese Patent Application No. 201610799332.X filed on Aug. 31, 2016. The contents of the above-listed applications are hereby incorporated by reference for all purposes.

TECHNICAL FIELD

The present disclosure relates to a flexible surgical instrument with structural backbones in a crossed arrangement, which belongs to the field of medical instrument.

BACKGROUND

In modern medical field, manual laparoscopic minimally invasive surgery (MIS) with several ports is clinically applied broadly. Such kind of MIS successfully reduces postoperative pains, complications, period for stay and recovery, as well as postoperative scars in appearance, for the patients. In order to further reduce surgical invasiveness, reduce the patient's pain, researchers have proposed a laparoscope MIS with a single port.

In contrast to the laparoscopic MIS with multi ports, which need to create several surface incisions, during the laparoscopic MIS with single port, all the surgical instruments enter into the abdominal cavity though one surface incision (typically umbilicus), thus further reduce trauma made to the patient. However, such a configuration of single port proposes more restricted requirements in terms of both design for the surgical instrument and the operation of the surgeon during surgery.

Traditional rigid surgical instruments are mostly elongated rod-like structure, with a surgical end effector provided at the tip of the instrument, and its movement is controlled by pulling wires or cables. For the manual laparoscope MIS with the single-port setup based on traditional rigid surgical instrument, because of the requirement on complex coordination between hands and eyes during operation, and in view of the difficulties that the surgical instrument has limited flexibility, and a narrow working range, the manual single-port laparoscopic MIS is yet not broadly clinically applied.

SUMMARY

In an embodiment, a flexible surgical instrument is provided, comprising: a distal structural body comprising first distal structural segment and second distal structural segment, the first distal structural segment comprising a first distal fixing disk and first distal segment structural backbones, the second distal structural segment comprising a second distal fixing disk and second distal segment structural backbones; and a proximal structural body comprising a proximal structural segment, the proximal structural segment comprising a proximal fixing disk, first proximal segment structural backbones, and second proximal segment structural backbones. The first proximal segment structural backbones are connected to the first distal segment structural backbones in a crossed arrangement, or the second proximal segment structural backbones are connected to the second distal segment structural backbones in a crossed arrangement.

In an embodiment, a flexible surgical instrument system is provided, comprising: a flexible surgical instrument, comprising: a distal structural body comprising first distal structural segment and second distal structural segment, the first distal structural segment comprising a first distal fixing disk and first distal segment structural backbones, the second distal structural segment comprising a second distal fixing disk and second distal segment structural backbones; and a proximal structural body comprising a proximal structural segment, the proximal structural segment comprising a proximal fixing disk, first proximal segment structural backbones, and second proximal segment structural backbones, the first proximal segment structural backbones being connected to the first distal segment structural backbones in a crossed arrangement; or the second proximal segment structural backbones being connected to the second distal segment structural backbones in a crossed arrangement; and a driving unit operable to turn the proximal structural segment.

DETAILED DESCRIPTION

The present disclosure will be described in detail in the followings with reference to the drawings and the embodiments.

Embodiment 1

Figure 1:
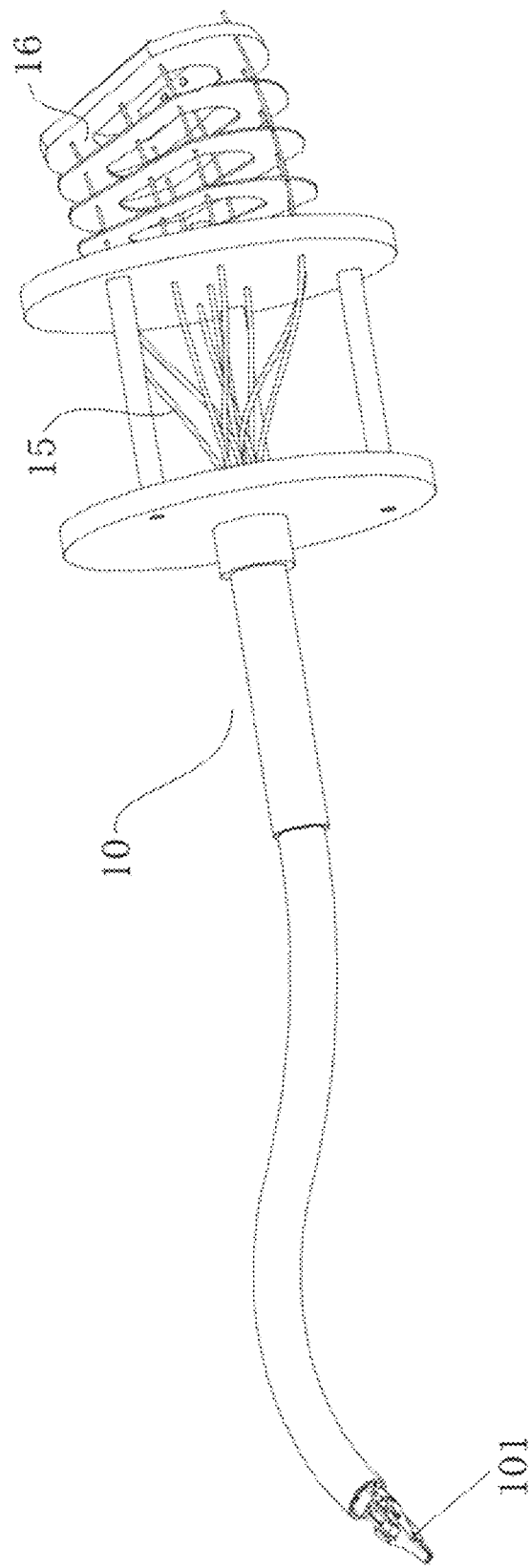
FIG. 1 is a schematic structural illustration of a flexible continuum structure of a flexible surgical instrument according to a first embodiment of the present disclosure.
Figure 2:
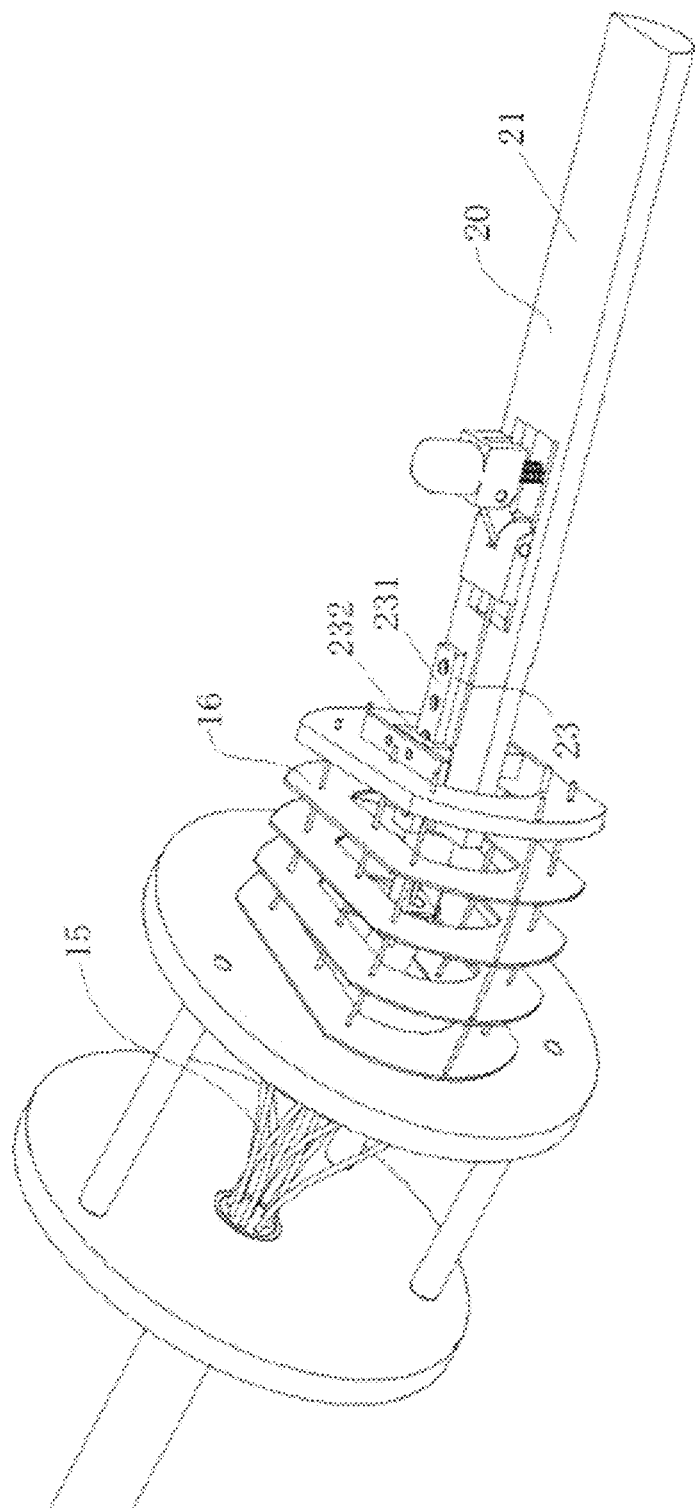
FIG. 2 is a schematic illustration of connection between a driving handle and the flexible continuum structure according to an embodiment of the present disclosure.

As shown in FIGS. 1, 2, a flexible surgical instrument of the embodiment includes a flexible continuum structure 10 and a driving handle 20.

Figure 3:
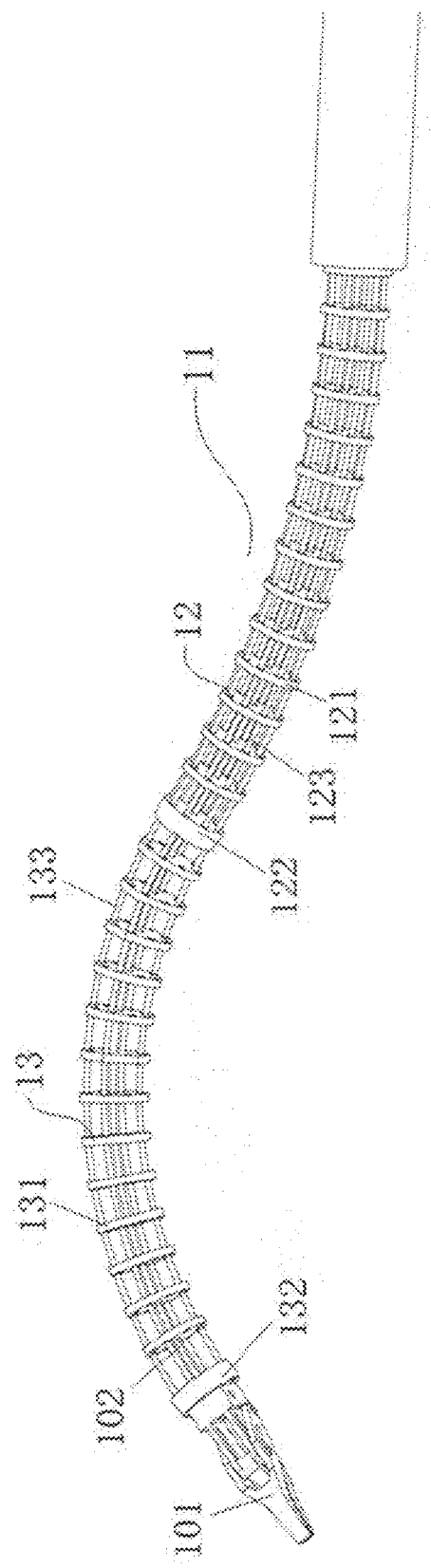
FIG. 3 is a structural schematic illustration of the distal structure of FIG. 1.
Figure 4:
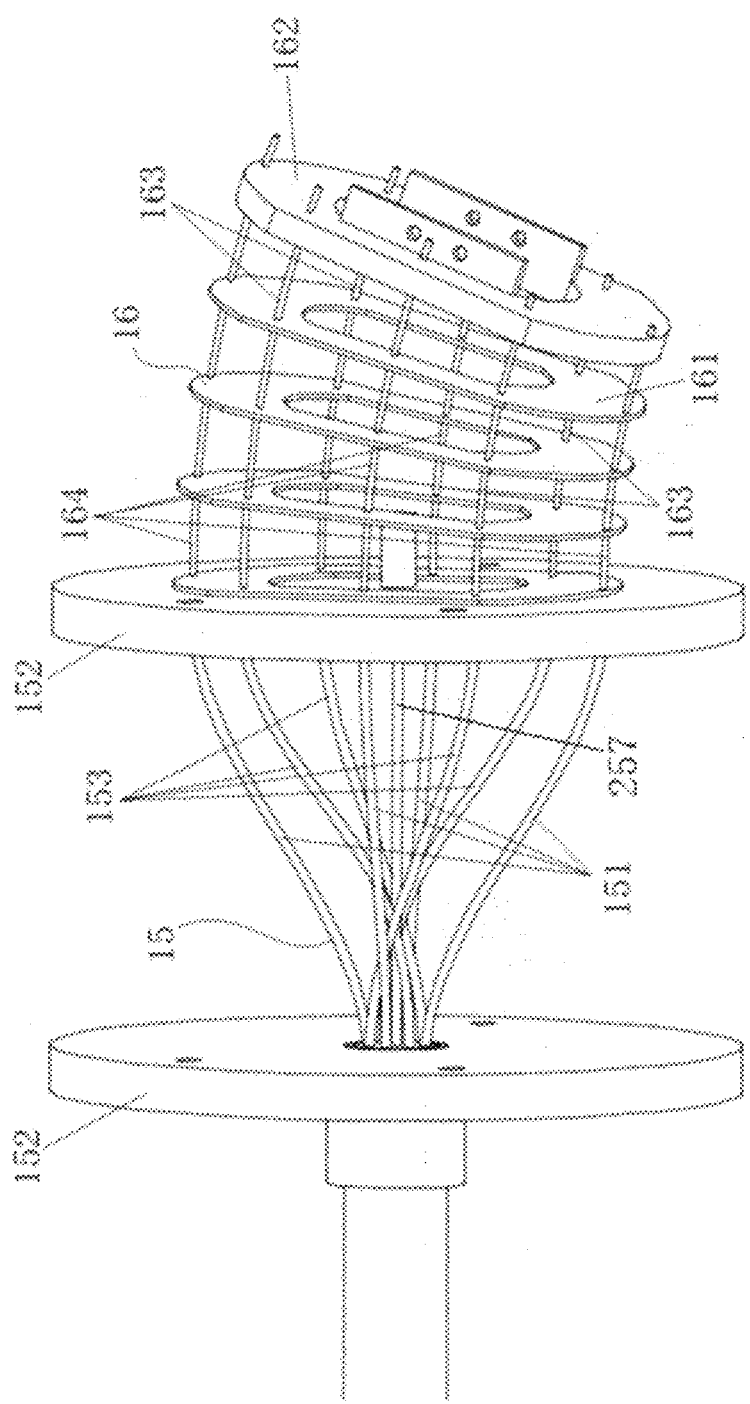
FIG. 4 is a structural schematic illustration of the proximal structure and the middle connection body of FIG. 1.

The flexible continuous body structure 10 includes a distal structural body 11 (as shown in FIG. 3), a proximal structural body 16 (as shown in FIG. 4) and a middle connection body 15. The distal structural body 11 includes a first distal segment 12 and a second distal segment 13 connected in series, the proximal structural body 16 includes a proximal segment. The proximal segment is associated to the first distal segment 12 and the second distal segment 13 by the middle connection body 15, when the proximal structural body 16 turns, the distal structural body 11 may be driven to turn correspondingly. The driving handle 20 is associated to the proximal structural body 16 for controlling turning of the proximal structural body 16.

The first distal segment 12 includes a first distal spacing disk 121, a first distal fixing disk 122 and first segment structural backbone(s) 123; the second distal segment 13 includes a second distal spacing disk 131, a second distal fixing disk 132 and second segment structural backbone(s) 132. Wherein, the first distal spacing disk 121 and the second distal spacing disk 131 are respectively spaced distributed within the first distal segment 12 and the second distal segment 13, which function to prevent the first segment structural backbone(s) 123 and the second segment structural backbone(s) 133 from being unstable when being pushed.

The proximal segment includes a proximal spacing disk 161, a proximal fixing disk 162, first segment structural backbone(s) 163 and second segment structural backbone(s) 164. Wherein, the proximal spacing disk 161 is spaced distributed within the proximal segment, which functions to prevent the first segment structural backbone(s) 163 and the second structural backbone(s) 164 from being unstable when being pushed. The first segment structural backbone(s) 163 on the proximal segment and the first structural backbone(s) 123 on the first distal segment 12 are fixedly connected respectively one to one or are of the same structural backbone; the second segment structural backbone(s) 164 on the proximal segment and the second structural backbone(s) 133 on the second distal segment 13 are fixedly connected respectively one to one or are of the same structural backbone. The number of the first segment structural backbone(s) 123 on the first distal segment 12 and the number of the second segment structural backbone(s) 133 on the second distal segment 13 are both more than three.

The middle connection body 15 includes passage fixing plate(s) 152, structural backbone guiding passage(s) 151 and structural backbone cross guiding passage(s) 153 fixedly connected between the passage fixing plates 152. One end of a first segment structural backbone(s) 163 (123) is fixedly connected to the proximal fixing disk 162, the other end thereof is fixedly connected to the first distal fixing disk 122 after extending through the proximal spacing disk 161, the structural backbone cross guiding passage(s) 153 and the first distal spacing disk 121 in sequence; one end of a second segment structural backbone(s) 164 (133) is fixedly connected to the proximal fixing disk 162, the other end thereof is fixedly connected to the second distal fixing disk 132 after extending through the proximal spacing disk 161, the structural backbone guiding passage(s) 151, the first distal segment 12 and the second distal spacing disk 131 in sequence. The structural backbone guiding passage(s) 151 and the structural backbone cross guiding passage(s) 153 function to remain the shape of the structural backbone(s) unchanged when the structural backbone(s) is pushed, pulled. Wherein, the structural cross guiding passage(s) 153 presents left-right cross in a horizontal direction or upper-lower cross in a vertical direction, so that the first segment structural backbone 163 at a left part of the proximal segment connects to a first segment structural backbone 123 at a right part of the first distal segment 12, and the first segment structural backbone 163 at a right part of the proximal segment connects to the first segment structural backbone 123 at the left part of the first distal segment 12; or the first segment structural backbone 163 at an upper part of the proximal segment connects to a first segment structural backbone 123 at a lower part of the first distal segment 12, and the first segment structural backbone 163 at a lower part of the proximal segment connects to the first segment structural backbone 123 at an upper part of the first distal segment 12.

When the structural backbone cross guide passage(s) 153 is in a crossed arrangement in horizontal direction, if the proximal structural body 16 turns along the horizontal direction, the first distal segment 12 will turn in the same direction along the horizontal direction with a certain proportion (determined collectively by a distance in horizontal direction between the first segment structural backbones 163 at the left and right parts of the proximal segment and a distance in horizontal direction between the first segment structural backbones 123 at the left and right parts of the first distal segment 12), the second distal segment 13 will turn in an opposite direction along the horizontal direction with a certain proportion (determined collectively by a distance in horizontal direction between the second segment structural backbones 164 at the left and right parts of the proximal segment and a distance in horizontal direction between the second segment structural backbones 133 at the left and right parts of the second distal segment 13); if the proximal structural body 16 turns along the vertical direction, the first distal segment 12 will turn in an opposite direction along the vertical direction with a certain proportion (determined collectively by a distance in vertical direction between the first segment structural backbones 163 at the upper and lower parts of the proximal segment and a distance in vertical direction between the first segment structural backbones 123 at the upper and lower parts of the first distal segment 12), the second distal segment 13 will turn in an opposite direction along the vertical direction with a certain proportion (determined collectively by a distance in vertical direction between the second segment structural backbones 164 at the upper and lower parts of the proximal segment and a distance in vertical direction between the second segment structural backbones 133 at the upper and lower parts of the second distal segment 13).

When the structural backbone cross guide passage(s) 153 is in a crossed arrangement in vertical direction, if the proximal structural body 16 turns along the horizontal direction, the first distal segment 12 will turn in an opposite direction along the horizontal direction with a certain proportion (determined collectively by a distance in horizontal direction between the first segment structural backbones 163 at the left and right parts of the proximal segment and a distance in horizontal direction between the first segment structural backbones 123 at the left and right parts of the first distal segment 12), the second distal segment 13 will turn in an opposite direction along the horizontal direction with a certain proportion (determined collectively by a distance in horizontal direction between the second segment structural backbones 164 at the left and right parts of the proximal segment and a distance in horizontal direction between the second segment structural backbones 133 at the left and right parts of the second distal segment 13); if the proximal structure 16 turns along the vertical direction, the first distal segment 12 will turn in the same direction along the vertical direction with a certain proportion (determined collectively by a distance in vertical direction between the first segment structural backbones 163 at the upper and lower parts of the proximal segment and a distance in vertical direction between the first segment structural backbones 123 at the upper and lower parts of the first distal segment 12), the second distal segment 13 will turn in an opposite direction along the vertical direction with a certain proportion (determined collectively by a distance in vertical direction between the second segment structural backbones 164 at the upper and lower parts of the proximal segment and a distance in vertical direction between the second segment structural backbones 133 at the upper and lower parts of the second distal segment 13).

Figure 5:
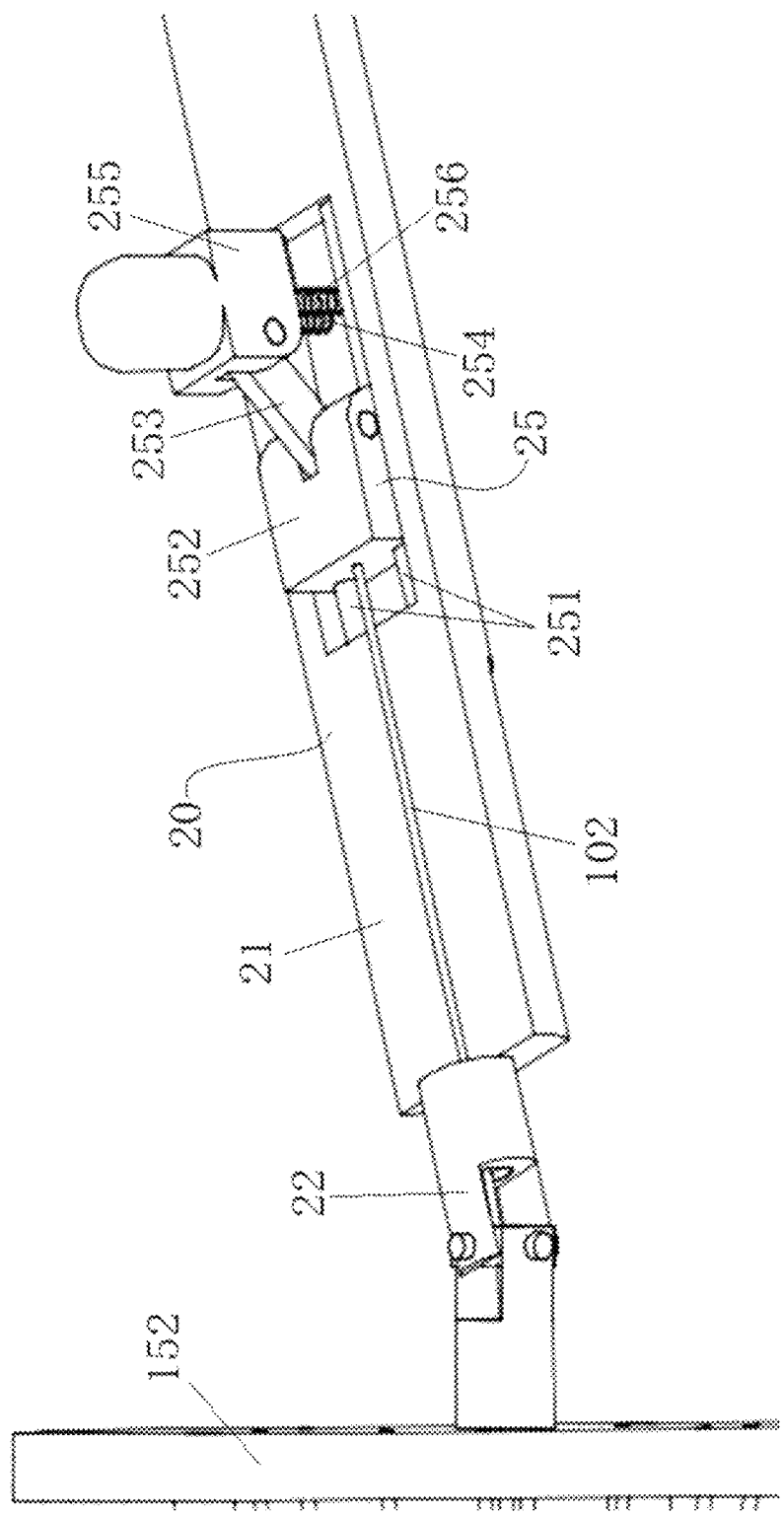
FIG. 5 is a structural schematic illustration of a driving handle according to an embodiment of the present disclosure.

As shown in FIGS. 2, 5, the driving handle 20 includes a driving handle base 21, a gimble 22 and a linear sliding module 23. Wherein, the driving handle base 21 extends through the proximal structure 16, and connects to the passage fixing plate 152 via the gimble 22, so that the driving handle base 21 is able to rotate towards any direction about a fixing point. The driving handle base 21 connects to the proximal fixing disk 162 via the linear sliding module 23, the linear sliding module 23 includes a track 231 and a slide 232 slidably connected on the track 231, wherein the track 231 is fixedly connected on the driving handle base 21, and the slide 232 connects with the proximal fixing disk 162. The linear sliding module 23 functions to allow a central axis of the proximal fixing disk 162 to be always coincide with a central axis of the driving handle 20, and enable the driving handle 20 to slide along the central axis of the proximal fixing disk 162, thus guaranteeing that when the driving handle 20 controls the proximal structural body 16 to turn, its shape of turning is approximately a circular arc.

Further, a surgical end effector 101 is provided at a front end of the distal structural body 11, control wire(s) 102 for the surgical end effector 101 extends through the distal structural body 11, and the other end thereof connects to a surgical end effector driving mechanism 25 provided on the driving handle base 21. The surgical end effector driving mechanism 25 includes a horizontal guide rod 251, a horizontal moving slider 252, a link 253, a vertical guide rod 254 and a vertical moving slider 255, wherein the vertical guide rod 254 is fixedly connected to the driving handle base 21 and is perpendicular to the axial direction of the driving handle base 21; the vertical moving slider 255 is slidably connected on the vertical guide rod 254; there are two horizontal guide rods 251 fixedly connected to the driving handle base 21 and distributed on two sides of the vertical guide rod 254, the horizontal guide rods 251 are parallel to the axial direction of the driving handle base 21. The two horizontal guide rods 251 together slidably support the horizontal moving slider 252, the horizontal moving slider 252 is located in front of the vertical guide rod 254. The vertical moving slider 255 connects to the horizontal moving slider 252 via the link 253. A spring 256 is sleeved on the vertical guide rod 254, one end of the spring 256 is fixedly connected to the driving handle base 21, and the other end thereof is fixedly connected to the vertical moving slider 255. The horizontal moving slider 252 is fixedly connected to the control wire(s) 102. When the vertical moving slider 255 is pressed down, the vertical moving slider 255 urges the horizontal moving slider 252 via the link 253 to move the horizontal moving slider forwardly along the horizontal guide rod 251, thus creating a push force on the control wire(s) 102, so as to drive the surgical end effector 101 (such as surgical forceps) to act. The control wire(s) 102 of the surgical end effector 101 can also transfer various kind of energy, such as electricity, high frequency vibration and the like, to execute electrical surgery.

Further, control wire guiding passage(s) 257 is also provided between the passage fixing plates 152, the control wire(s) 102 extends through the control wire guiding passage(s) 257, the control wire guiding passage(s) 257 functions to prevent the control wire(s) 102 from being unstable when being pushed.

Figure 6:
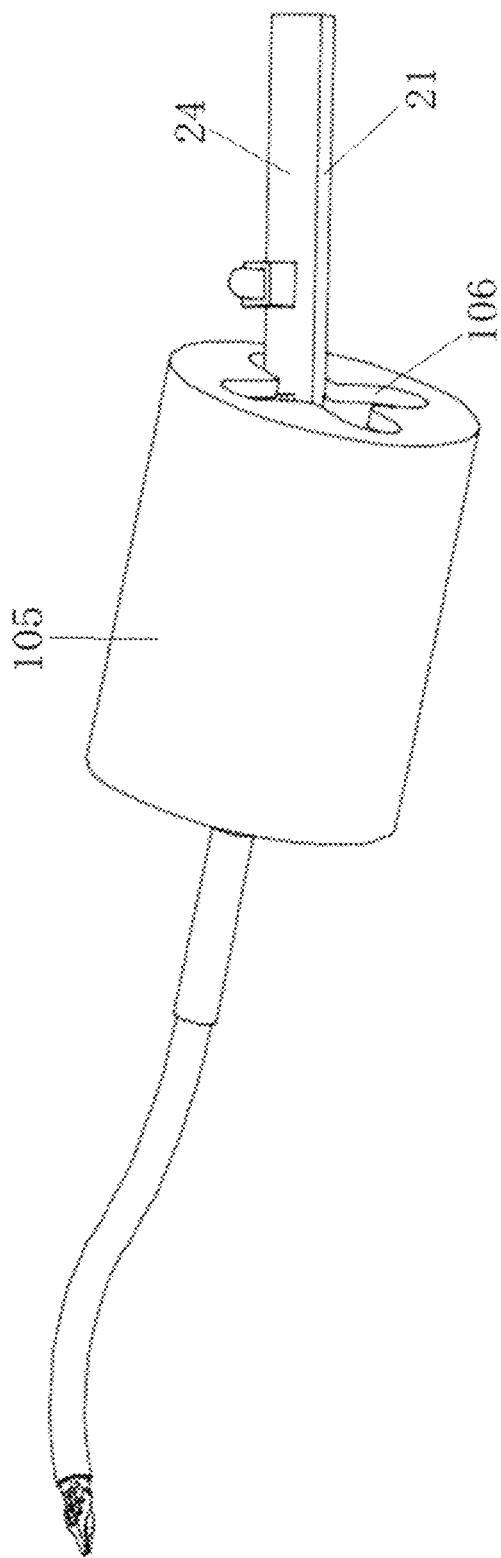
FIG. 6 is a structural schematic illustration of the flexible surgical instrument according to the first embodiment of the present disclosure, after the surgical instrument is mounted with a flexible surgical instrument housing.
Figure 7:
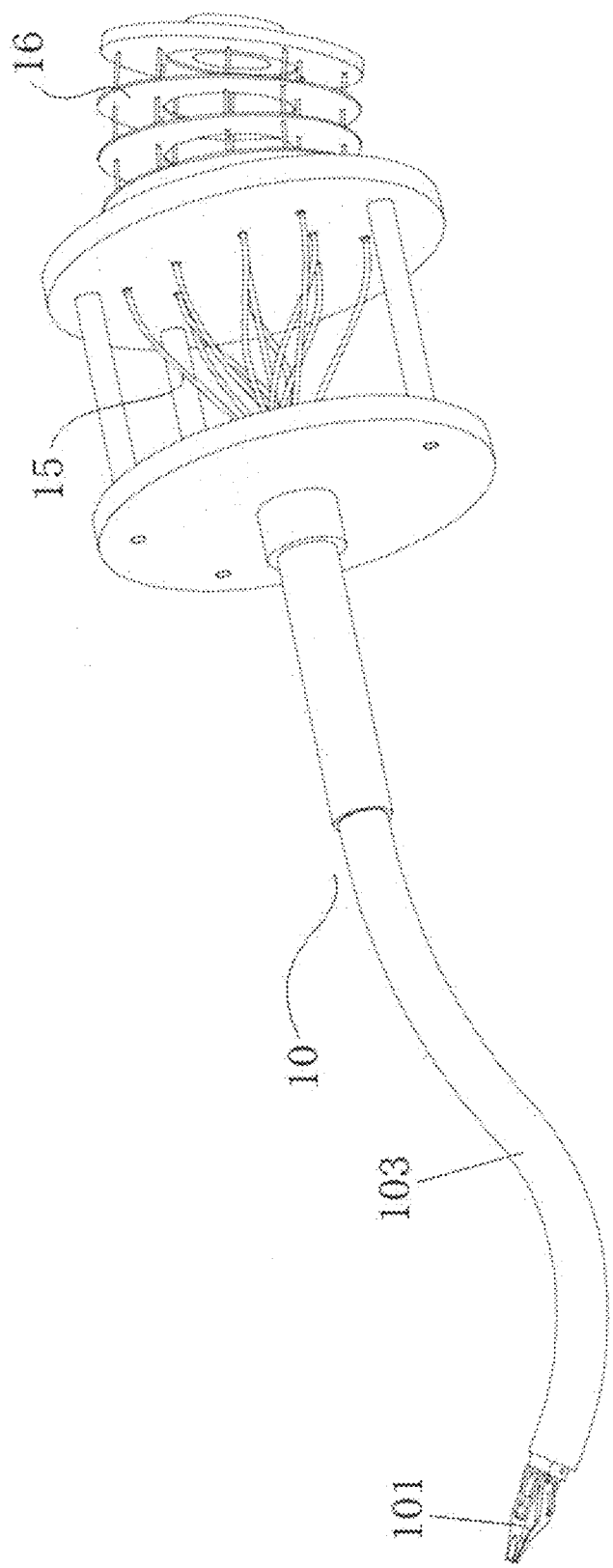
FIG. 7 is a schematic structural illustration of a flexible continuum structure of a flexible surgical instrument according to a second embodiment of the present disclosure.

Further, as shown in FIG. 6, the present disclosure also includes a driving handle cover 24 and a flexible surgical instrument housing 105. Wherein, the driving handle cover 24 is fixedly connected to the driving handle base 21 to form an enclosed handle profile. The middle connections body 15 and the proximal structural body 16 are both located within the flexible surgical instrument housing 105, the passage fixing plate 152 is fixedly connected to the flexible surgical instrument housing 105. A cross-shaped chute 106 is provided at a rear end of the flexible surgical instrument housing 105, the driving handle 20 is rotatable along the chute 106, i.e. rotate in the horizontal direction and in the vertical direction, respectively. Besides, when the driving handle 20 is rotated, the rotation movement can be transferred to the passage fixing plate 152 via the gimble 22, thus in turn rotates the whole flexible surgical instrument, realizing control on a rolling angle of the surgical end effector 101. Further, the chute 105 of the present disclosure can also be designed as various shapes according to various moving requirements.

Embodiment 2

This embodiment differs from Embodiment 1 in that the first segment structural backbone(s) 163 (123) extends through the structural backbone guiding passage(s) 151, and the second segment structural backbone(s) 164 (133) extends through the structural backbone cross guiding passage(s) 153. The structures of the rest portion are identical to those in Embodiment 1.

Embodiment 3

As shown in FIGS. 7-11, this embodiment includes a flexible continuum structure 10a and a driving handle 20.

Figure 9:
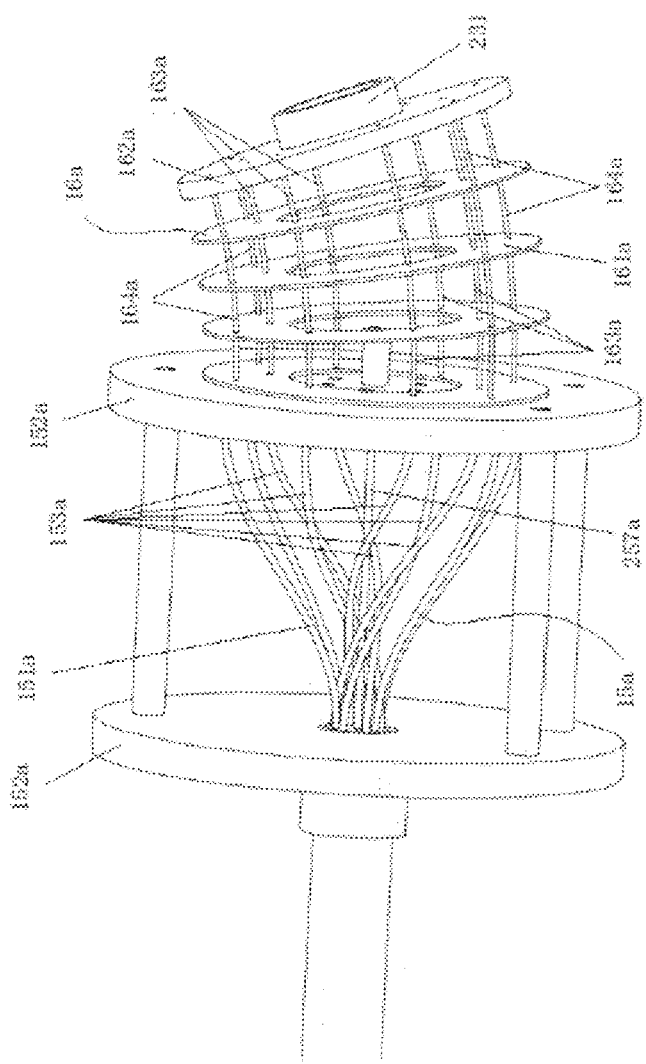
FIG. 9 is a structural schematic illustration of the proximal structure and the middle connection body of an embodiment of the present disclosure.
Figure 10:
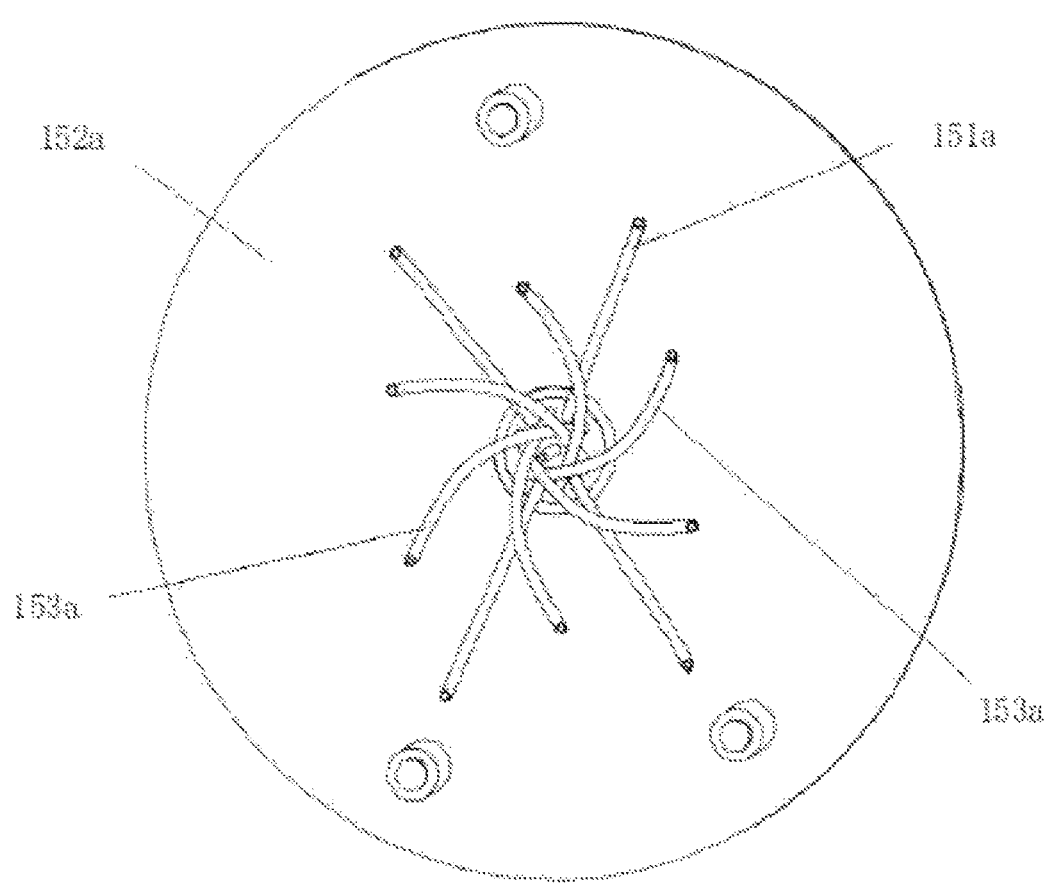
FIG. 10 is a structural schematic illustration of the middle connection body of FIG. 9.

The flexible continuum structure 10 includes a distal structure 11 (can be identical to the preceding embodiments, see FIG. 3), a proximal structural body 16a (as shown in FIG. 9) and a middle connection body 15a. The distal structural body 11 includes a first distal segment 12 and a second distal segment 13 connected in series, the proximal structural body 16a includes a proximal segment. The proximal segment is associated to the first distal segment 12 and the second distal segment 13 by the middle connection body 15a, when the proximal structural body 16a turns, the distal structural body 11 may be driven to turn correspondingly. The driving handle 20a is associated to the proximal structural body 16a for controlling turning of the proximal structural body 16a.

The first distal segment 12 includes a first distal spacing disk 121, a first distal fixing disk 122 and first segment structural backbone(s) 123; the second distal segment 13 includes a second distal spacing disk 131, a second distal fixing disk 132 and second segment structural backbone(s) 132. Wherein, the first distal spacing disk 121 and the second distal spacing disk 131 are respectively spaced distributed within the first distal segment 12 and the second distal segment 13, which function to prevent the first segment structural backbone(s) 123 and the second segment structural backbone(s) 133 from being unstable when being pushed.

The proximal segment includes a proximal spacing disk 161a, a proximal fixing disk 162a, first segment structural backbone(s) 163a and second segment structural backbone (s) 164a. Wherein, the proximal spacing disk 161a is spaced distributed within the proximal segment, which functions to prevent the first segment structural backbone(s) 163a and the second structural backbone(s) 164a from being unstable when being pushed. The first segment structural backbone(s) 163a on the proximal segment and the first structural backbone(s) 123 on the first distal segment 12 are fixedly connected respectively one to one or are of the same structural backbone; the second segment structural backbone(s) 164a on the proximal segment and the second structural backbone(s) 133 on the second distal segment 13 are fixedly connected respectively one to one or are of the same structural backbone. The number of the first segment structural backbone(s) 123 on the first distal segment 12 and the number of the second segment structural backbone(s) 133 on the second distal segment 13 are both more than three.

The middle connection body 15a includes passage fixing plate(s) 152a, structural backbone guiding passage(s) 151a and structural backbone cross guiding passage(s) 153a fixedly connected between the passage fixing plates 152a. One end of first segment structural backbone(s) 163a (123) is fixedly connected to the proximal fixing disk 162a, the other end thereof is fixedly connected to the first distal fixing disk 122 after extending through the proximal spacing disk 161a, the structural backbone cross guiding passage(s) 153a and the first distal spacing disk 121 in sequence; one end of a second segment structural backbone(s) 164a (133) is fixedly connected to the proximal fixing disk 162a, the other end thereof is fixedly connected to the second distal fixing disk 132 after extending through the proximal spacing disk 161a, the structural backbone guiding passage(s) 151a, the first distal segment 12 and the second distal spacing disk 131 in sequence. The structural backbone guiding passage(s) 151a and the structural backbone cross guiding passage(s) 153a function to remain the shape of the structural backbone (s) unchanged when the structural backbone(s) is pushed, pulled. Wherein, the structural backbone cross guiding passages 153a are distributed in central symmetry (as shown in FIG. 9), and the structural backbone cross guiding passages 153a are arranged in opposed crossed arrangement around the distribution center, so that the first segment structural backbone 163a at one part of the proximal segment connects to the first segment structural backbone 123 at one part of the first distal segment 12, thus realizing that when the proximal structural body 16 is driven to turn in any direction, the first distal segment 12 turns in the same direction correspondingly.

The structural backbone guiding passage(s) 153a of this embodiment is arranged in opposed crossed arrangement around the distribution center, when the proximal structural body 16a turns in a certain direction, the first distal segment 12 will turn in the same direction with a certain proportion (the proportion is determined collectively by a distribution radius of the first segment structural backbones 163a in the proximal segment and a distribution radius of the first structural backbones 123 in the first distal segment 12), and the second distal segment 13 will turn in an opposite direction with a certain proportion (the proportion is determined collectively by a distribution radius of the second segment structural backbones 164a in the proximal segment and a distribution radius of the second segment structural backbones 133 in the second distal segment 13).

Figure 8:
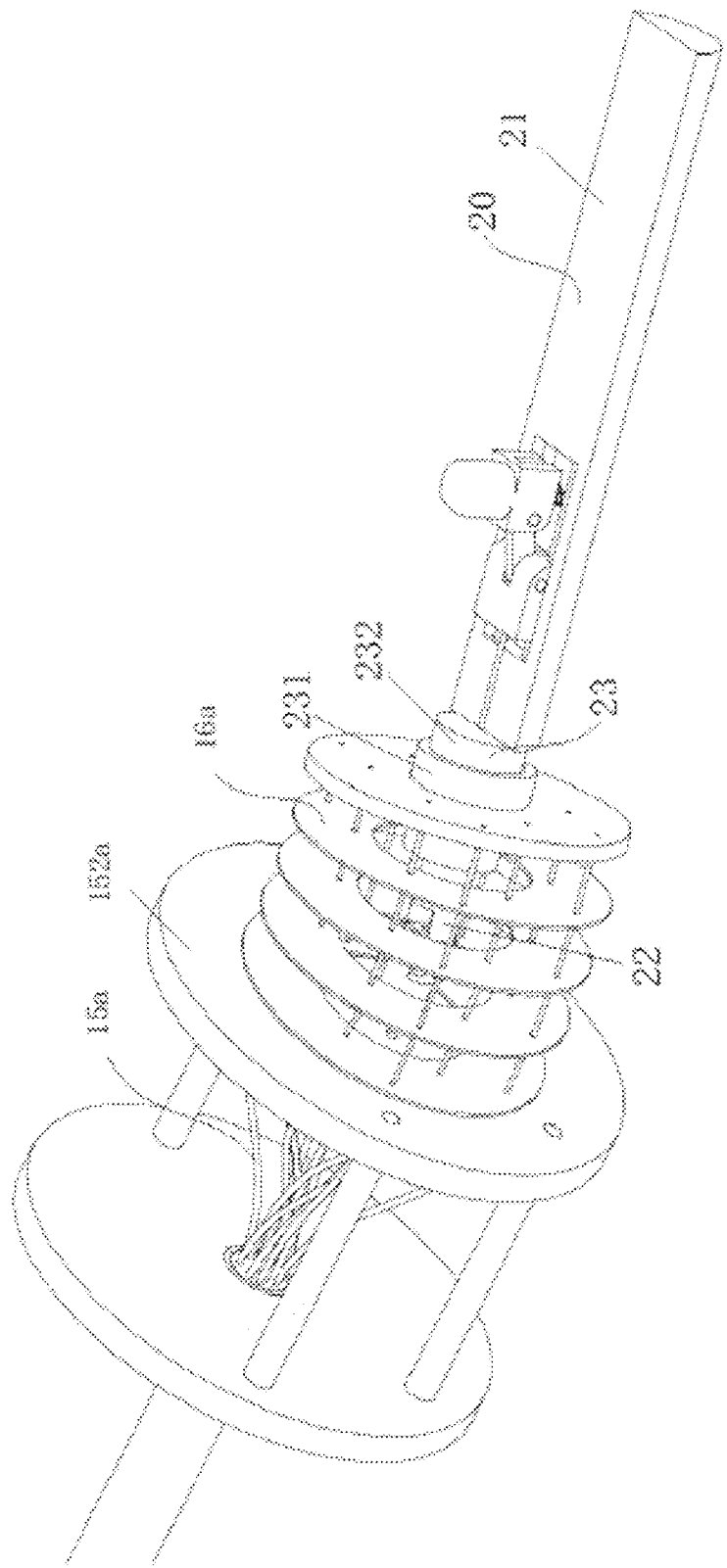
FIG. 8 is a schematic illustration of connection between a driving handle and the flexible continuum structure according to another embodiment of the present disclosure.

As shown in FIGS. 5, 8, the driving handle 20 includes a driving handle base 21, a gimble 22 and a linear sliding module 23. Wherein, the driving handle base 21 is connected to the proximal fixing disk 162a via the linear sliding module 23, the linear sliding module 23 includes a guide bush 231 fixedly provided at a center of the proximal fixing disk 162a and a cylindrical slider 232 slidably connected in the guide bush 231. One end of the cylindrical slider 232 is fixedly connected to the driving handle base 21, the other end thereof is connected to the passage fixing plates 152a via the gimble 22, so that the driving handle base 21; the vertical moving slider 255 is slidably connected on the vertical guide rod 254; there are two horizontal guide rods 251 fixedly connected to the driving handle base 21 and distributed on two sides of the vertical guide rod 254, the horizontal guide rods 251 are parallel to the axial direction of the driving handle base 21. The two horizontal guide rods 251 together slidably support the horizontal moving slider 252, the horizontal moving slider 252 is located in front of the vertical guide rod 254. The vertical moving slider 255 connects to the horizontal moving slider 252 via the link 253. A spring 256 is sleeved on the vertical guide rod 254, one end of the spring 256 is fixedly connected to the driving handle base 21, and the other end thereof is fixedly connected to the vertical moving slider 255. The horizontal moving slider 252 is fixedly connected to the control wire(s) 102. When the vertical moving slider 255 is pressed down, the vertical moving slider 255 urges the horizontal moving slider 252 via the link 253 to move the horizontal moving slider forwardly along the horizontal guide rod 251, thus creating a push force on the control wire(s) 102, so as to drive the surgical end effector 101 (such as surgical forceps) to act. The control wire(s) 102 of the surgical end effector 101 can also transfer various kind of energy, such as electricity, high frequency vibration and the like, to execute electrical surgery.

Further, as shown in FIG. 9, control wire guiding passage (s) 257a is also provided between the passage fixing plates 152a, the control wire(s) 102 extends through the control wire guiding passage(s) 257a, the control wire guiding passage(s) 257a functions to prevent the control wire(s) 102 from being unstable when being pushed.

Figure 11:
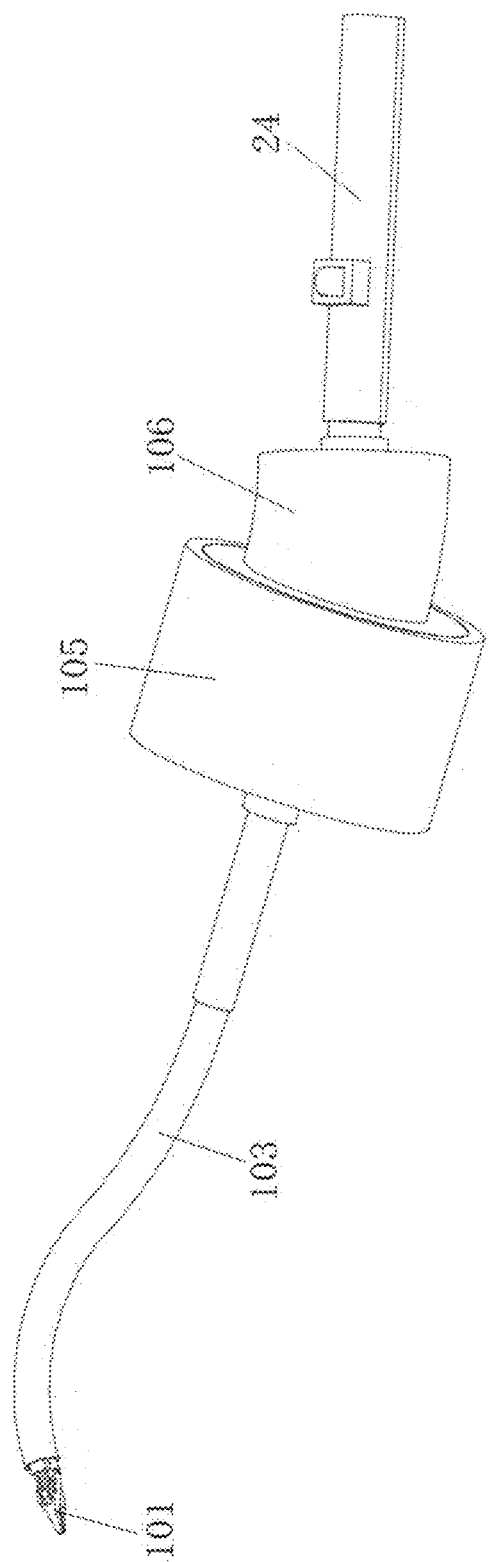
FIG. 11 is a structural schematic illustration of the flexible surgical instrument according to the present disclosure, after the surgical instrument is mounted with a flexible surgical instrument housing.

Further, as shown in FIG. 11, the present disclosure also includes a driving handle cover 24 and a flexible surgical instrument housing 105. Wherein, the driving handle cover 24 is fixedly connected to the driving handle base 21 to form an enclosed handle profile. The middle connections body 15a is located within the flexible surgical instrument housing 105, the passage fixing plates 152a is fixedly connected to the flexible surgical instrument housing 105. Besides, when the driving handle 20 is rotated, the rotation movement can be transferred to the passage fixing plates 152a via the gimble 22, thus in turn rotates the whole flexible surgical instrument, realizing control on a rolling angle of the surgical end effector 101.

Further, as shown in FIG. 11, a proximal structural body skin 106 covers outside the proximal structural body 16, a skin 103 covers outside the distal structural body 11. The skins 103, 106 functions to improve appearance, and can improve surface smoothness of the distal structural body 11.

Embodiment 4

This embodiment differs from Embodiment 1 in that the first segment structural backbone(s) 163a (123) extends through the structural backbone guiding passage 151a, and the second segment structural backbone(s) 164a (133) extends through the structural backbone cross guiding passage 153a. The structures of the rest portion are identical to those in Embodiment 1.

In an embodiment, one object of the present disclosure is providing a flexible surgical instrument with structural backbones in a crossed arrangement, the flexible surgical instrument can be well applied in surgeries carried out through a single surgical incision or a plurality of surgical incisions.

In an embodiment, the present application proposes the following solution: A flexible surgical instrument with structural backbones in a crossed arrangement, the flexible surgical instrument including a flexible continuous body structure comprising a distal structural body, a proximal structural body and a middle connecting body; the distal structural body includes a first distal segment and a second distal segment; the first distal segment includes a first distal spacing disk, a first distal fixing disk and first segment; the second distal segment includes a second distal spacing disk, a second distal fixing disk and a second segment structural backbone(s); the proximal structural body includes a proximal segment including a proximal spacing disk, a proximal fixing disk, first segment structural backbone(s) and a second segment structural backbone; the first segment structural backbone(s) located on the proximal segment and the first segment structural backbone located on the first distal segment are fixedly connected respectively one to one or are of the same structural backbone; the second segment structural backbone located on the proximal segment and the second segment structural backbone located on the second distal segment are fixedly connected respectively one to one or are of the same structural backbone; the middle connecting body includes two passage fixing plates, structural backbone guiding passage(s) and structural backbone cross guiding passage(s) are fixedly connected between the two passage fixing plates; one end of the first segment structural backbone(s) are fixedly connected to the proximal fixing disk, and the other end thereof is fixedly connected to the first distal fixing disk after passing through the proximal spacing disk, the structural backbone cross guiding passage(s) and the first distal spacing disk in sequence; one end of the second segment structural backbone(s) is fixedly connected to the proximal fixing disk, and the other end thereof is fixedly connected to the second distal fixing disk after passing through the proximal spacing disk, the structural backbone guiding passage(s), the first distal segment and the second distal spacing disk; the structural backbone cross guiding passage(s) is in left and right crossing arrangement in a horizontal direction, or in an upper and down crossing arrangement in a vertical direction, so that the first segment structural bond at the left part of the proximal segment connects with the first segment structural backbone at the right part of the first distal segment, and the first segment structural backbone at the right part of the proximal segment connects with the first segment structural backbone at the left part of the first distal segment, or the first segment structural backbone at the upper part of the proximal segment connects with the first segment structural backbone at the lower part of the first distal segment, and the first segment structural backbone at the lower part of the proximal segment connects with the first segment structural backbone at the upper part of the first distal segment.

In an embodiment, the flexible surgical instrument may further include a driving handle including a driving handle base, a gimbal and a linear sliding module; the driving handle base passes through the proximal structural body and connects to the passage fixing plates via the gimbal; the driving handle base connects to the proximal fixing disk via the linear sliding module.

In an embodiment, the linear sliding module includes a track and a slider slidably connected on the track, the track is fixedly connected on the driving handle base, the slider is fixedly connected to the proximal fixing disk.

In an embodiment, a surgical end effector is provided at a front end of the distal structural body, control wire(s) for the surgical end effector extends through the distal structural body, the other end connects to a surgical end effector driving mechanism provided on the driving handle base.

In an embodiment, the surgical end effector driving mechanism includes a horizontal guide rod, a horizontal moving slider, a link, a vertical guide rod and a vertical moving slider, wherein the vertical guide rod is fixedly connected to the driving handle base and is perpendicular to the axial direction of the driving handle base, the vertical moving slider is slidably connected to the vertical guide rod, the horizontal guide rod is fixedly connected to the driving handle base and is parallel to the axial direction of the driving handle base, the horizontal moving slider is slidably connected to the horizontal guide rod, the horizontal moving slider is located in front of the vertical guide rod, the vertical moving slider connects to the horizontal moving slider via the link; a spring is sleeved on the vertical guide rod, one end of the spring is fixedly connected to the driving handle base, and the other end thereof is fixedly connected to the vertical moving slider; the horizontal moving slider is fixedly connected to one end of the control wire(s).

In an embodiment, control wire guiding passage(s) is provided between the passage fixing plates, the control wire(s) extends through the control wire guiding passage(s).

In an embodiment, the flexible surgical instrument may further comprises a driving handle cover and a flexible surgical instrument housing; the driving handle cover is fixedly connected to the driving handle base; the middle connection body and the proximal structural body both locate within the flexible surgical instrument housing, the passage fixing plates are fixedly connected to the flexible surgical instrument housing; a chute for rotation of the driving handle is provided at a rear end of the flexible surgical instrument housing.

In an embodiment, the chute is in cross shape.

The present disclosure further provides a flexible surgical instrument with structural backbones in a crossed arrangement, the flexible surgical instrument including a flexible continuous body structure comprising a distal structural body, a proximal structural body and a middle connecting body; the distal structural body includes a first distal segment and a second distal segment; the first distal segment includes a first distal spacing disk, a first distal fixing disk and a first segment structural backbone; the second distal segment includes a second distal spacing disk, a second distal fixing disk and a second segment structural backbone; the proximal structural body includes a proximal segment including a proximal spacing disk, a proximal fixing disk, first segment structural backbone(s) and second segment structural backbone; the first segment structural backbone located on the proximal segment and the first segment structural backbone located on the first distal segment are fixedly connected respectively one to one or are of the same structural backbone; the second segment structural backbone located on the proximal segment and the second segment structural backbone located on the second distal segment are fixedly connected respectively one to one or are of the same structural backbone; the middle connecting body includes two passage fixing plates, structural backbone guiding passage(s) and structural backbone cross guiding passage(s) are fixedly connected between the two passage fixing plates; one end of the first segment structural backbone(s) is fixedly connected to the proximal fixing disk, and the other end thereof is fixedly connected to the first distal fixing disk after passing through the proximal spacing disk, the structural backbone cross guiding passage(s) and the first distal spacing disk in sequence; one end of the second segment structural backbone(s) is fixedly connected to the proximal fixing disk, and the other end thereof is fixedly connected to the second distal fixing disk after passing through the proximal spacing disk, the structural backbone guiding passage(s), the first distal segment and the second distal spacing disk; the structural backbone cross guiding passage(s) is in left and right crossing arrangement in a horizontal direction, or in an upper and down crossing arrangement in a vertical direction, so that the second segment structural bond at the left part of the proximal segment connects with the second segment structural backbone at the right part of the second distal segment, and the second segment structural backbone at the right part of the proximal segment connects with the second segment structural backbone at the left part of the second distal segment, or the second segment structural backbone at the upper part of the proximal segment connects with the second segment structural backbone at the lower part of the first distal segment, and the second segment structural backbone at the lower part of the proximal segment connects with the second segment structural backbone at the upper part of the second distal segment.

In an embodiment, the flexible surgical instrument may further include a driving handle including a driving handle base, a gimbal and a linear sliding module; the driving handle base passes through the proximal structural body and connects to the passage fixing plates via the gimbal; the driving handle base connects to the proximal fixing disk via the linear sliding module.

The present disclosure further provides a flexible surgical instrument with structural backbones in opposed and crossed arrangement, including a flexible continuous body structure comprising a distal structural body, a proximal structural body and a middle connection body; the distal structural body includes a first distal segment including a first distal spacing disk, a first distal fixing disk and a first segment structural backbone, and a second distal segment including a second distal spacing disk, a second distal fixing disk and a second segment structural backbone; the proximal structural body includes a proximal segment including a proximal spacing disk, a proximal fixing disk, first segment structural backbone(s) and second segment structural backbone(s); the first segment structural backbone on the proximal segment and the first segment structural backbone on the first distal segment are fixedly connected respectively one to one or are of the same structural backbone; the second segment structural backbone on the proximal segment and the second segment structural backbone on the second distal segment are fixedly connected respectively one to one or are of the same structural backbone; the middle connection body includes two passage fixing plates, between which structural backbone guiding passage(s) and structural backbone cross guiding passage(s) are connected; one end of the first segment structural backbone(s) is fixedly connected to the proximal fixing disk, and the other end thereof is fixedly connected to a first distal fixing disk after passing through the proximal spacing disk, the structural backbone cross guiding passage(s) and the first distal spacing disk in sequence; one end of the second segment structural backbone(s) is fixedly connected to the proximal fixing plate, and the other end thereof is fixedly connected to the second distal fixing disk after passing through the proximal spacing disk, the structural backbone guiding passage(s), the first distal segment and the second distal spacing disk in sequence; and The structural backbone cross guiding passages are in opposed and crossed arrangement about the distribution center.

In an embodiment, the flexible surgical instrument may further includes a driving handle comprising a driving handle base, a gimble and a linear sliding module; the linear sliding module includes a guide bush fixedly provided at a center of the proximal fixing disk and a cylindrical slide slidably connected in the guide bush, one end of the cylindrical slide is fixedly connected to the driving handle base, and the other end thereof is connected to the passage fixing plates via the gimble.

In an embodiment, a surgical end effector is provided at a front end of the distal structural body, control wire(s) for the surgical end effector extends through the distal structural body, the other end connects to a surgical end effector driving mechanism provided on the driving handle base.

In an embodiment, the surgical end effector driving mechanism includes a horizontal guide rod, a horizontal moving slider, a link, a vertical guide rod and a vertical moving slider, wherein the vertical guide rod is fixedly connected to the driving handle base and is perpendicular to the axial direction of the driving handle base, the vertical moving slider is slidably connected to the vertical guide rod, the horizontal guide rod is fixedly connected to the driving handle base and is parallel to the axial direction of the driving handle base, the horizontal moving slider is slidably connected to the horizontal guide rod, the horizontal moving slider is located in front of the vertical guide rod, the vertical moving slider connects to the horizontal moving slider via the link; a spring is sleeved on the vertical guide rod, one end of the spring is fixedly connected to the driving handle base, and the other end thereof is fixedly connected to the vertical moving slider; the horizontal moving slider is fixedly connected to one end of the control wire(s).

In an embodiment, control wire guiding passage(s) is provided between the passage fixing plates, the control wire(s) extends through the control wire guiding passage(s).

In an embodiment, the flexible surgical instrument may further includes a driving handle cover and a flexible surgical instrument housing; the driving handle cover is fixedly connected to the driving handle base; the middle connection body is located within the flexible surgical instrument housing, the passage fixing plates are fixedly connected to the flexible surgical instrument housing.

The present disclosure still further provides a flexible surgical instrument with structural backbones in opposed and crossed arrangement, the flexible surgical instrument includes a flexible continuum structure comprising a distal structural body, a proximal structure and a middle connection body; the distal structure includes a first distal segment including a first distal spacing disk, a first distal fixing disk and a first segment structural backbone, and a second distal segment including a second distal spacing disk, a second distal fixing disk and a second segment structural backbone; the proximal structure includes a proximal segment including a proximal spacing disk, a proximal fixing disk, first segment structural backbone(s) and second segment structural backbone(s); the first segment structural backbone on the proximal segment and the first segment structural backbone on the first distal segment are fixedly connected respectively one to one or are of the same structural backbone; the second segment structural backbone on the proximal segment and the second segment structural backbone on the second distal segment are fixedly connected respectively one to one or are of the same structural backbone; the middle connection body includes two passage fixing plates, between which structural backbone guiding passage(s) and structural backbone cross guiding passage(s) are connected; one end of the first segment structural backbone(s) is fixedly connected to the proximal fixing disk, and the other end thereof is fixedly connected to a first distal fixing disk after passing through the proximal spacing disk, the structural backbone guiding passage(s) and the first distal spacing disk in sequence; one end of the second segment structural backbone(s) is fixedly connected to the proximal fixing disk, and the other end thereof is fixedly connected to the second distal fixing disk after passing through the proximal spacing disk, the structural backbone cross guiding passage(s), the first distal segment and the second distal spacing disk in sequence; and The structural backbone cross guiding passages are in opposed and crossed arrangement around a distribution center.

Thanks to the above mentioned technical solutions utilized in the present disclosure, the present disclosure has the advantages that 1) The present disclosure utilizes a continuum structure including a proximal structure, a middle connection body and a distal structure as the main body, wherein the distal structure is associated with the proximal structure via the middle connection body, the proximal structure is associated with the driving handle, thus when the driving handle drives the proximal structure to turn in any direction, the distal structure will turns correspondingly, realizing willful turning movements of the flexible surgical arm. 2) The distal structure, the middle connection body and the proximal structure of the present disclosure utilize redundant structural backbone arrangement (the number of the structural backbone(s) is greater than three), which improves stability and loading capacity of the system. 3) The present disclosure is provided with structural backbone cross guiding passage(s) in the middle connection body, so that the first segment structural backbone(s) is in a crossed arrangement in the horizontal (vertical) direction, thereby realizing the effect that when the proximal structure is driven to turn in the horizontal (vertical) direction, the first distal segment correspondingly turns in the same direction, the second distal segment correspondingly turns in an opposite direction; and when the proximal structure is driven to turn in the vertical (horizontal) direction, the first distal segment and the second distal segment both correspondingly turn in an opposite direction. 4) In the present disclosure, a surgical end effector is provided on a front end of the distal structural body, control wire(s) of the surgical end effector extends through the distal structural body, connects to a surgical end effector driving mechanism located on the driving handle base, thus the surgical end effector may realize control on the action of the surgical end effector by means of pushing and pulling the control wire(s).

The present disclosure can be applied in multi-port laparoscopic surgery, as well as in single-port laparoscopic surgery.

The present disclosure is described only by the above embodiments, the structure, providing position and connection of the parts can be varied. Based on the technical solutions of the present disclosure, the modification or equivalent variations on the individual parts based on the principle of the present disclosure shall not be excluded from the protective scope of the present disclosure.

The invention claimed is:
1. A flexible surgical instrument, comprising:
a distal structural body comprising first distal structural segment and second distal structural segment, the first distal structural segment comprising a first distal fixing disk and first distal segment structural backbones, the second distal structural segment comprising a second distal fixing disk and second distal segment structural backbones;
a proximal structural body comprising a proximal structural segment, the proximal structural segment comprising a proximal fixing disk, first proximal segment structural backbones, and second proximal segment structural backbones, the first proximal segment structural backbones being connected to the first distal segment structural backbones in a crossed arrangement; or the second proximal segment structural backbones being connected to the second distal segment structural backbones in a crossed arrangement; and
a driving handle connected to the proximal structural segment and to turn the proximal structural segment, wherein the driving handle comprises:
a driving handle base passing through the proximal structural segment and rotationally disposed at a distal end of the proximal structural segment; and
a linear sliding module slidably connecting the proximal fixing disk to the driving handle base, to allow the driving handle to drive the proximal fixing disk to turn by sliding axially relative to the proximal fixing disk, thereby turning the proximal structural segment.

2. The flexible surgical instrument of claim 1, wherein the proximal structural segment is operable to turn the first distal structural segment and the second distal structural in different directions.

3. The flexible surgical instrument of claim 1, wherein:
proximal ends of the first proximal segment structural backbones are connected to the proximal fixing disk, and distal ends of the first distal segment structural backbones are connected to the first distal fixing disk; and
proximal ends of the second proximal segment structural backbones are connected to the proximal fixing disk, and the second distal segment structural backbones pass through the first distal structural segment, distal ends of the second distal segment structural backbones are connected to the second distal fixing disk.

4. The flexible surgical instrument of claim 1, further comprising a middle connection body comprising:
a first passage fixing plate close to the distal structural body;
a second passage fixing plate close to the proximal structural body; and structural backbone cross guiding passages disposed between the first passage fixing plate and the second passage fixing plate, wherein the first distal segment structural backbones pass through the structural backbone cross guiding passages, or the second distal segment structural backbones pass through the structural backbone cross guiding passages.

5. The flexible surgical instrument of claim 4, the middle connection body further comprises:

structural backbone guiding passages disposed between the first passage fixing plate and the second passage fixing plate, wherein the first distal segment structural backbones pass through the structural backbone guiding passages and the second distal segment structural backbones pass through the structural backbone cross guiding passages; or the second distal segment structural backbones pass through the structural backbone guiding passages and the first distal segment structural backbones pass through the structural backbone cross guiding passages.

6. The flexible surgical instrument of claim 4, wherein the structural backbone cross guiding passages are in left-right cross arrangement in a horizontal direction or in upper-lower cross arrangement in a vertical direction.

7. The flexible surgical instrument of claim 4, wherein the structural backbone cross guiding passages are in cross-arrangement in a direction around a distribution center.

8. The flexible surgical instrument of claim 1, further comprising a fixing plate disposed between the distal structural body and the proximal structural body;

wherein the driving handle further comprises a gimble disposed at the fixing plate and connected to the driving handle base.

9. The flexible surgical instrument of claim 1, wherein the linear sliding module comprises:

a track connected on the driving handle base; and a slider slidably connected to the track and connected to the proximal fixing disk.

10. The flexible surgical instrument of claim 1, further comprising:

a flexible surgical instrument housing, the proximal structural body being disposed in the flexible surgical instrument housing; and a chute for rotation of the driving handle, the chute being disposed at a proximal end of the flexible surgical instrument housing.

11. The flexible surgical instrument of claim 1, further comprising:

a surgical end effector disposed at a distal end of the distal structural body;

a surgical end effector driving mechanism; and a control wire passing through the distal structural body, the control wire comprising a proximal end connected to the surgical end effector driving mechanism and a distal end connected to the surgical end effector.

12. The flexible surgical instrument of claim 11, further comprising:

a driving handle connected to the proximal structural segment and to turn the proximal structural segment, and wherein the surgical end effector driving mechanism is disposed at a driving handle base of the driving handle.

13. The flexible surgical instrument of claim 12, wherein the surgical end effector driving mechanism comprises:

a horizontal guide rod connected to the driving handle base; and a horizontal moving slider slidably connected to the horizontal guide rod, wherein the proximal end of the control wire is connected to the horizontal moving slider.

14. The flexible surgical instrument of claim 13, wherein the surgical end effector driving mechanism comprises:

a vertical guide rod connected to the driving handle base;

a vertical moving slider slidably connected to the vertical guide rod; and a link rod comprising a first end rotatably connected to the horizontal moving slider and a second end rotatably connected to the vertical moving slider, respectively.

15. The flexible surgical instrument of claim 14, wherein the surgical end effector driving mechanism comprises:

a spring sleeved on the vertical guide rod and comprising a first end connected to driving handle base and a second end connected to the vertical moving slider.

16. A flexible surgical instrument system, comprising:

a flexible surgical instrument, comprising:

a distal structural body comprising first distal structural segment and second distal structural segment, the first distal structural segment comprising a first distal fixing disk and first distal segment structural backbones, the second distal structural segment comprising a second distal fixing disk and second distal segment structural backbones;

a proximal structural body comprising a proximal structural segment, the proximal structural segment comprising a proximal fixing disk, first proximal segment structural backbones, and second proximal segment structural backbones, the first proximal segment structural backbones being connected to the first distal segment structural backbones in a crossed arrangement; or the second proximal segment structural backbones being connected to the second distal segment structural backbones in a crossed arrangement;

a driving handle connected to the proximal structural segment and to turn the proximal structural segment, wherein the driving handle comprises:

a driving handle base passing through the proximal structural segment and rotationally disposed at a distal end of the proximal structural segment; and a linear sliding module slidably connecting the proximal fixing disk to the driving handle base, to allow the driving handle to drive the proximal fixing disk to turn by sliding axially relative to the proximal fixing disk, thereby turning the proximal structural segment; and a driving unit operable to turn the driving handle.

17. The flexible surgical instrument system of claim 16, further comprising a middle connection body comprising:

a first passage fixing plate close to the distal structural body;

a second passage fixing plate close to the proximal structural body; and structural backbone cross guiding passages disposed between the first passage fixing plate and the second passage fixing plate, wherein the first distal segment structural backbones pass through the structural backbone cross guiding passages, or the second distal segment structural backbones pass through the structural backbone cross guiding passages.

18. The flexible surgical instrument system of claim 17, the middle connection body further comprises:

structural backbone guiding passages disposed between the first passage fixing plate and the second passage fixing plate, wherein the first distal segment structural backbones pass through the structural backbone guiding passages and the second distal segment structural backbones pass through the structural backbone cross guiding passages; or the second distal segment structural backbones pass through the structural backbone guiding passages and the first distal segment structural backbones pass through the structural backbone cross guiding passages.

* * * * *